(12) United States Patent
Zhang et al.

(10) Patent No.: US 12,207,947 B2
(45) Date of Patent: *Jan. 28, 2025

(54) SYSTEMS AND METHODS FOR IMAGE CORRECTION

(71) Applicant: SHANGHAI UNITED IMAGING HEALTHCARE CO., LTD., Shanghai (CN)

(72) Inventors: Shuangyue Zhang, Shanghai (CN); Tuoyu Cao, Houston, TX (US); Hui Liu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 12 days.

This patent is subject to a terminal disclaimer.

(21) Appl. No.: 18/161,861

(22) Filed: Jan. 30, 2023

(65) Prior Publication Data

US 2023/0172557 A1 Jun. 8, 2023

Related U.S. Application Data

(63) Continuation of application No. 16/870,948, filed on May 9, 2020, now Pat. No. 11,564,631.

(30) Foreign Application Priority Data

Aug. 29, 2019 (CN) .......................... 201910810494.2

(51) Int. Cl.
*A61B 5/055* (2006.01)
*A61B 5/00* (2006.01)
(Continued)

(52) U.S. Cl.
CPC ............ *A61B 5/721* (2013.01); *A61B 5/0035* (2013.01); *A61B 5/055* (2013.01); *A61B 6/037* (2013.01);
(Continued)

(58) Field of Classification Search
CPC ..................................................... A61B 5/721
See application file for complete search history.

(56) References Cited

U.S. PATENT DOCUMENTS 7,945,079 B2 5/2011 Rosen
9,398,855 B2 7/2016 Miao et al.
(Continued)

FOREIGN PATENT DOCUMENTS

CN 107730567 A 2/2018
WO WO-2012176114 A1 * 12/2012 ........... A61B 5/1128

*Primary Examiner* — Oneal R Mistry
(74) *Attorney, Agent, or Firm* — METIS IP LLC

(57) ABSTRACT

The present disclosure provides a system and method for motion field generation and image correction. The method may include obtaining a plurality of first sets of magnetic resonance (MR) image data of an object generated based on a plurality of first sets of imaging sequences. The method may include obtaining a motion curve of the object. The method may include obtaining position emission tomography (PET) image data of the object generated in a scanning time period. The method may include generating one or more target motion fields corresponding to the scanning time period based on the plurality of first sets of MR image data and the motion curve. The method may include generating one or more corrected PET images by correcting, based on the one or more target motion fields, the PET image data.

20 Claims, 9 Drawing Sheets

(51) Int. Cl.
- *A61B 6/00* (2006.01)
- *A61B 6/03* (2006.01)
- *G01R 33/48* (2006.01)
- *G06T 7/00* (2017.01)
- *G06T 11/00* (2006.01)

(52) U.S. Cl.
CPC ............ *A61B 6/5247* (2013.01); *A61B 6/527* (2013.01); *G01R 33/481* (2013.01); *G06T 7/0012* (2013.01); *G06T 11/008* (2013.01); *G06T 2207/10088* (2013.01); *G06T 2207/10104* (2013.01); *G06T 2207/30048* (2013.01); *G06T 2207/30168* (2013.01); *G06T 2210/41* (2013.01)

(56) References Cited

U.S. PATENT DOCUMENTS

| | | | |
|---|---|---|---|
| 9,535,145 | B2 | 1/2017 | Demeester et al. |
| 9,778,382 | B2 | 10/2017 | Fenchel et al. |
| 9,990,741 | B2 | 6/2018 | Panin |
| 10,267,884 | B2 | 4/2019 | Bauer et al. |
| 2012/0265050 | A1* | 10/2012 | Wang ............... A61B 6/485 600/407 |
| 2013/0274590 | A1* | 10/2013 | Auboiroux ......... A61B 90/361 600/411 |
| 2014/0153806 | A1* | 6/2014 | Glielmi ............. A61B 6/037 382/131 |
| 2014/0355855 | A1* | 12/2014 | Miao ............. G01R 33/56509 382/131 |
| 2017/0091963 | A1 | 3/2017 | Panin |
| 2021/0059555 | A1* | 3/2021 | Buchwald ............ A61B 5/113 |
| 2022/0361767 | A1* | 11/2022 | Buchwald ............ A61B 5/055 |

* cited by examiner

SYSTEMS AND METHODS FOR IMAGE CORRECTION

CROSS-REFERENCE TO RELATED APPLICATIONS

This application is a continuation of U.S. application Ser. No. 16/870,948 filed on May 9, 2020, which claims priority to Chinese Patent Application No. 201910810494.2, filed on Aug. 29, 2019, the contents of each of which are hereby incorporated by reference in its entirety.

TECHNICAL FIELD

The present disclosure generally relates to image technology, and more particularly to systems and methods for motion field generation and image correction.

BACKGROUND

With the development of imaging technology, various techniques are combined for disease diagnoses. For example, a multi-modality system (e.g., a positron emission tomography (PET) system combined with a magnetic resonance imaging (MRI) system) can be used to exam soft tissue. However, the image quality of images (e.g., images of chest and/or abdomen) generated by the PET-MRI system is generally affected by a motion (e.g., respiratory motion, heartbeat, etc.) of a scanned object. Exemplary motion artifact correction techniques may include a reconstruction technique guided by a motion waveform generated from a respiratory belt or a navigator, a correction technique based on a motion field that is generated based on special MRI sequence(s), or the like. However, the reconstruction technique guided by the motion waveform can only reconstruct a corrected image corresponding to a specific respiratory phase or state, without using image data of other respiratory phases or states, thereby resulting in a relatively low signal-to-noise ratio (SNR) of the corrected image. The correction technique based on special MRI sequence(s) may make full use of the image data generated in different respiratory phases or states, and achieve motion artifact correction between different respiratory phases or states, thereby ensuring the image quality. However, the correction technique based on special MRI sequence(s) relies on the special MRI sequence(s), and can only perform motion artifact correction for image data acquired during a period in which the special MRI sequence(s) are used. Accordingly, other image data acquired during other periods in which the special MRI sequence(s) are not used may not be efficiently corrected. If the motion field generated based on the special MRI sequence(s) is used to correct the other image data acquired during the other periods, the other image data may not be efficiently corrected as the motion of the scanned object may be unstable. Therefore, it is desirable to provide systems and methods for generating motion field(s) and correcting images efficiently.

SUMMARY

In one aspect of the present disclosure, a method for motion field generation and image correction is provided. The method may include one or more operations. The one or more operations may be implemented on a computing device having one or more processors and one or more storage devices. The one or more processors may obtain a plurality of first sets of magnetic resonance (MR) image data of an object generated based on a plurality of first sets of imaging sequences. The plurality of first sets of imaging sequences may be separated in a scanning time period. The one or more processors may obtain a motion curve of the object. The motion curve may be associated with a physiological motion of the object in the scanning time period. The one or more processors may obtain positron emission tomography (PET) image data of the object generated in the scanning time period. The one or more processors may generate one or more target motion fields corresponding to the scanning time period based on the plurality of first sets of MR image data and the motion curve. The one or more processors may generate one or more corrected PET images by correcting, based on the one or more target motion fields, the PET image data.

In some embodiments, the method may further include obtaining a plurality of second sets of MR image data of the object generated based on a plurality of second sets of imaging sequences. The plurality of second sets of imaging sequences may be interleaved with the plurality of first sets of imaging sequences.

In some embodiments, the method may include generating one or more corrected MR images by correcting, based on the one or more target motion fields, the plurality of second sets of MR image data.

In some embodiments, the plurality of first sets of imaging sequences may be sparsely interspersed between the plurality of second sets of imaging sequences.

In some embodiments, the motion curve may include at least one of a respiratory motion curve or a cardiac motion curve.

In some embodiments, a generation of at least a portion of the PET image data may be simultaneous to a generation of the plurality of first sets of MR image data.

In some embodiments, the PET image data may include PET raw data or data corresponding to one or more PET images reconstructed based on the PET raw data.

In some embodiments, for generating one or more target motion fields corresponding to the scanning time period, the method may include obtaining a plurality of first sets of motion fields by generating, based on the motion curve, at least one first set of motion fields corresponding to each first set of time intervals in which one first set of MR image data among the plurality of first sets of MR image data are generated. In some embodiments, the method may include generating the one or more target motion fields based on the plurality of first sets of motion fields.

In some embodiments, the motion curve may include a respiratory motion curve. In some embodiments, for generating, based on the motion curve, at least one first set of motion fields corresponding to each first set of time intervals in which one first set of MR image data among the plurality of first sets of MR image data is generated, the method may include determining a plurality of respiratory phases of a respiratory motion of the object. The method may include determining a plurality of pieces of MR image data corresponding to the plurality of respiratory phases by determining, based on the plurality of first sets of MR image data and the respiratory motion curve, a piece of MR image data corresponding to each of the plurality of respiratory phases. The method may include reconstructing a plurality of images corresponding to the plurality of respiratory phases based on the plurality of pieces of MR image data. The method may include generating the at least one first set of motion fields based on the plurality of images corresponding to the plurality of respiratory phases.

In some embodiments, for determining a plurality of respiratory phases of a respiratory motion of the object, the method may include may include determining a plurality of first sets of time intervals in which the plurality of first sets of MR image data are generated. The method may include determining at least one portion of the respiratory motion curve corresponding to the plurality of first sets of time intervals. The method may include determining the plurality of respiratory phases of the respiratory motion of the object based on the at least one portion of the respiratory motion curve.

In some embodiments, for determining a plurality of pieces of MR image data corresponding to the plurality of respiratory phases, the method may include dividing the plurality of first sets of MR image data into the plurality of pieces of MR image data corresponding to the plurality of respiratory phases, based on the plurality of first sets of MR image data and the plurality of respiratory phases.

In some embodiments, for generating the one or more target motion fields based on the plurality of first sets of motion fields, the method may include determining, based on the scanning time period and a plurality of first sets of time intervals in which the plurality of first sets of MR image data are generated, a plurality of second sets of time intervals. The method may include obtaining a plurality of second sets of motion fields by generating, based on the plurality of first sets of motion fields, at least one second set of motion fields corresponding to each second set of time intervals of the plurality of second sets of time intervals. The method may include generating the one or more target motion fields based on the plurality of first sets of motion fields and the plurality of second sets of motion fields.

In some embodiments, for generating, based on the plurality of first sets of motion fields, at least one second set of motion fields corresponding to each second set of time intervals of the plurality of second sets of time intervals, the method may include designating one or more first sets of motion fields corresponding to one of the plurality of first sets of time intervals that is adjacent to the each second set of time intervals as the at least one second set of motion fields.

In some embodiments, for generating, based on the plurality of first sets of motion fields, at least one second set of motion fields corresponding to each second set of time intervals of the plurality of second sets of time intervals, the method may include generating the at least one second set of motion fields corresponding to the each second set of time intervals by fitting one or more first sets of motion fields corresponding to two of the plurality of first sets of time intervals that are adjacent to the each second set of time intervals.

In some embodiments, for generating the one or more target motion fields based on the plurality of first sets of motion fields and the plurality of second sets of motion fields, the method may include designating the plurality of first sets of motion fields and the plurality of second sets of motion fields as the one or more target motion fields.

In some embodiments, for generating the one or more target motion fields based on the plurality of first sets of motion fields, the method may include generating the one or more target motion fields by fitting the plurality of first sets of motion fields.

In some embodiments, the each first set of time intervals may include one or more respiratory cycles of the object.

In some embodiments, the plurality of first sets of imaging sequences may include at least one of a multi-cycle radial imaging sequence, a spiral imaging sequence, a random imaging sequence, or a radial imaging sequence with a golden-angle scheme.

In another aspect of the present disclosure, a system for motion field generation and image correction is provided. The system may include at least one storage device storing a set of instructions, and at least one processor in communication with the storage device. When executing the set of instructions, the at least one processor may be configured to cause the system to perform operations. The operation may include obtaining a plurality of first sets of magnetic resonance (MR) image data of an object generated based on a plurality of first sets of imaging sequences. The plurality of first sets of imaging sequences may be separated in a scanning time period. The operation may include obtaining a motion curve of the object. The motion curve may be associated with a physiological motion of the object in the scanning time period. The operation may include obtaining positron emission tomography (PET) image data of the object generated in the scanning time period. The operation may include generating one or more target motion fields corresponding to the scanning time period based on the plurality of first sets of MR image data and the motion curve. The operation may include generating one or more corrected PET images by correcting, based on the one or more target motion fields, the PET image data.

In still another aspect of the present disclosure, a non-transitory computer-readable medium storing at least one set of instructions is provided. When executed by at least one processor, the at least one set of instructions may direct the at least one processor to perform a method. The method may include obtaining a plurality of first sets of magnetic resonance (MR) image data of an object generated based on a plurality of first sets of imaging sequences. The plurality of first sets of imaging sequences may be separated in a scanning time period. The method may include obtaining a motion curve of the object. The motion curve may be associated with a physiological motion of the object in the scanning time period. The method may include obtaining positron emission tomography (PET) image data of the object generated in the scanning time period. The method may include generating one or more target motion fields corresponding to the scanning time period based on the plurality of first sets of MR image data and the motion curve. The method may include generating one or more corrected PET images by correcting, based on the one or more target motion fields, the PET image data. physiological motion of the object in the scanning time period. The method may include obtaining positron emission tomography (PET) image data of the object generated in the scanning time period. The method may include generating one or more target motion fields corresponding to the scanning time period based on the plurality of first sets of MR image data and the motion curve. The method may include generating one or more corrected PET images by correcting, based on the one or more target motion fields, the PET image data.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 2:
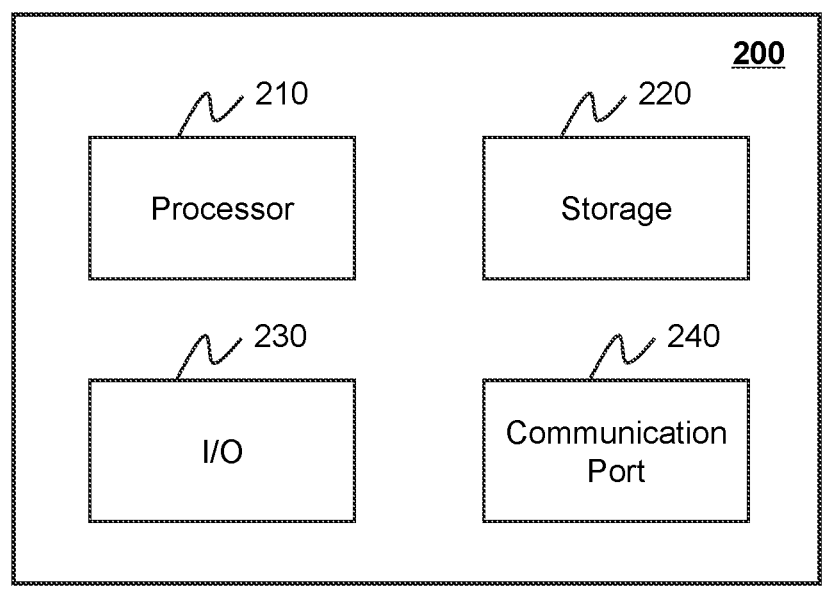
FIG. 2 is a schematic diagram illustrating exemplary hardware and/or software components of an exemplary computing device on which the processing device may be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

As used herein, a representation of an object (e.g., a patient, or a portion thereof) in an image may be referred to the object for brevity. For instance, a representation of an organ or tissue (e.g., the heart, the liver, a lung, etc., of a patient) in an image may be referred to as the organ or tissue for brevity. As used herein, an operation on a representation of an object in an image may be referred to as an operation on the object for brevity. For instance, a segmentation of a portion of an image including a representation of an organ or tissue (e.g., the heart, the liver, a lung, etc., of a patient) from the image may be referred to as a segmentation of the organ or tissue for brevity.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

A positron emission computed tomography (PET) device or system may exam metabolic activity of an object based on an aggregation of a substance (injected into the object) in metabolism. The PET technology may be a relatively efficient imaging technology for clinical diagnoses in the field of nuclear medicine. Using the PET technology, one or more radioactive tracer isotopes (also referred to as radionuclides) (e.g., 18F, 11C, etc.) may be injected into the object to label one or more substances (e.g., glucose, proteins, nucleic acids, fatty acids, etc.) of the object. The radionuclides may release positrons in a process of decay. A positron may move a certain distance (e.g., from tenths of a millimeter to one or more millimeters) and/or annihilate when encountering an electron. Accordingly, a pair of photons having an energy of 511 KeV and opposite directions may be generated. The pair of photons may be captured by a highly sensitive detector to generate image data, and then scatter correction and/or random correction may be performed on the image data. A plurality of positrons may be collected and/or processed similarly, and three-dimensional (3D) images of the object may be obtained, thereby facilitating diagnoses of the object.

In magnetic resonance imaging (MRI), the object may be placed in a magnetic field, and a radio frequency (RF) pulse may be used to excite hydrogen nuclei in the object, thereby causing resonance of the hydrogen nuclei, and absorbing energy. After the RF pulse is removed, the hydrogen nuclei may emit signals at a specific frequency, and release the absorbed energy. The released energy may be recorded by a receiver in vitro, and an image may be generated. The image may be referred to as a nuclear magnetic resonance image. The magnetic resonance imaging (MRI) device or system may introduce no damage of ionizing radiation to the object, and may have many outstanding characteristics (e.g., multiple parameters, large amount of information, multi-directional imaging, high resolution of soft tissue, etc.). The MRI technology may be widely used in clinical diagnoses of diseases, and become an indispensable detection technique for some specific lesions.

A combination of the PET technology and the MRI technology may achieve synchronous data acquisition and image fusion, obtain more accurate information about the structure(s), function(s), and metabolism of the scanned object, and reduce or eliminate radiation received by the scanned object. Therefore, the combination of PET and MRI may be of a great value for improving the efficiency and/or accuracy of the diagnoses and treatments of diseases.

The present disclosure relates to systems and methods for image correction. It should be noted that the descriptions of image correction for PET image(s) and/or MRI image(s) in the present disclosure are merely provided for the purposes of illustration, and not intended to limit the scope of the present disclosure. In some embodiments, a plurality of first sets of magnetic resonance (MR) image data of an object generated based on a plurality of first sets of imaging sequences may be obtained. The plurality of first sets of imaging sequences may be separated in a scanning time period. In some embodiments, a motion curve of the object may be obtained. The motion curve may be associated with a physiological motion of the object in the scanning time period. In some embodiments, positron emission tomography (PET) image data of the object generated in the scanning time period may be obtained. In some embodiments, one or more target motion fields corresponding to the scanning time period may be generated based on the plurality of first sets of MR image data and the motion curve. In some embodiments, one or more corrected PET images may be generated by correcting, based on the one or more target motion fields, the PET image data.

In some embodiments, a whole-stage motion field corresponding to the entire scanning time period may be generated based on the one or more target motion fields. In some embodiments, the whole-stage motion field may include the one or more target motion fields. According to the present disclosure, the whole-stage motion field corresponding to the entire scanning time period may be generated stably through sparsely interspersing the plurality of first sets of imaging sequences. Besides, the systems and methods may correct the motion artifact(s) in PET images and/or MRI images generated in the entire scanning time period using the whole-stage motion field, and improve the image quality without increasing the scanning time of the PET images and/or MRI images or with increasing a small amount of the scanning time of the PET images and/or MRI images that hardly affects the object, and without being influenced by unstable physiological motions of the object.

Figure 1:
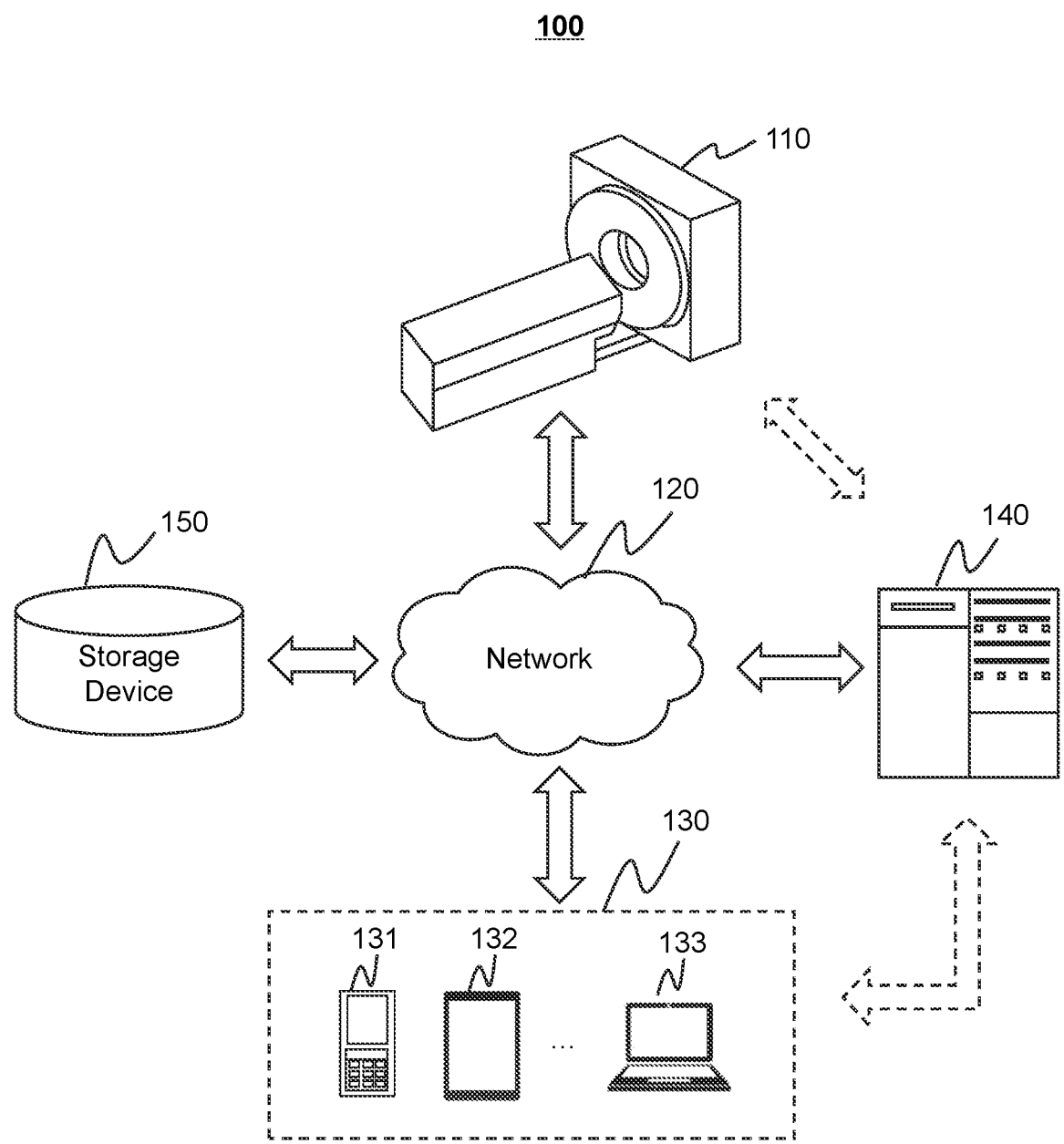
FIG. 1 is a schematic diagram illustrating an exemplary image processing system according to some embodiments of the present disclosure.

FIG. 1 is a schematic diagram illustrating an exemplary image processing system according to some embodiments of the present disclosure. The image processing system 100 may include a scanner 110, a network 120, one or more terminals 130, a processing device 140, and a storage device 150. The components in the image processing system 100 may be connected in one or more of various ways. Merely by way of example, the scanner 110 may be connected to the processing device 140 through the network 120. As another example, the scanner 110 may be connected to the processing device 140 directly as indicated by the bi-directional arrow in dotted lines linking the scanner 110 and the processing device 140. As still another example, the storage device 150 may be connected to the processing device 140 directly or through the network 120. As still another example, the terminal 130 may be connected to the processing device 140 directly (as indicated by the bi-directional arrow in dotted lines linking the terminal 130 and the processing device 140) or through the network 120.

The scanner 110 may generate or provide image(s) via scanning a subject or a part of the subject. In some embodiments, the scanner 110 may be a medical imaging device, for example, a positron emission tomography (PET) device, a single-photon emission computed tomography (SPECT) device, a magnetic resonance imaging (MRI) device, or the like, or any combination thereof. In some embodiments, the scanner 110 may include a multi-modality scanner. The multi-modality scanner may include a positron emission tomography-magnetic resonance imaging (PET-MRI) scanner, a SPET-MRI scanner, or the like, or any combination thereof. The multi-modality scanner may perform multi-modality imaging simultaneously. For example, the PET-MRI scanner may generate MRI data and PET data simultaneously in a single scan.

In some embodiments, the subject may include a body, substance, or the like, or any combination thereof. In some embodiments, the subject may include a specific portion of a body, such as a head, a thorax, an abdomen, or the like, or any combination thereof. In some embodiments, the subject may include a specific organ, such as a breast, a stomach, a gallbladder, a small intestine, a colon, etc. In some embodiments, the subject may include a physical model (also referred to as a mockup). The physical model may include one or more materials constructed as different shapes and/or dimensions. Different parts of the physical model may be made of different materials. Different materials may have different X-ray attenuation coefficients, different tracer isotopes, and/or different hydrogen proton contents. Therefore, different parts of the physical model may be recognized by the image processing system 100. In the present disclosure, "object" and "subject" are used interchangeably. In some embodiments, the scanner 110 may include a scanning table. The subject may be placed on the scanning table for imaging.

In some embodiments, the scanner 110 may transmit the image(s) via the network 120 to the processing device 140, the storage device 150, and/or the terminal(s) 130. For example, the image(s) may be sent to the processing device 140 for further processing or may be stored in the storage device 150.

The network 120 may include any suitable network that can facilitate the exchange of information and/or data for the image processing system 100. In some embodiments, one or more components of the image processing system 100 (e.g., the scanner 110, the terminal 130, the processing device 140, the storage device 150) may communicate information and/or data with one or more other components of the image processing system 100 via the network 120. For example, the processing device 140 may obtain one or more images from the scanner 110 via the network 120. As another example, the processing device 140 may obtain one or more images from the storage device 150 via the network 120. As a further example, the processing device 140 may obtain user instructions from the terminal 130 via the network 120. The network 120 may be and/or include a public network (e.g., the Internet), a private network (e.g., a local area network (LAN), a wide area network (WAN))), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the image processing system 100 may be connected to the network 120 to exchange data and/or information.

Figure 3:
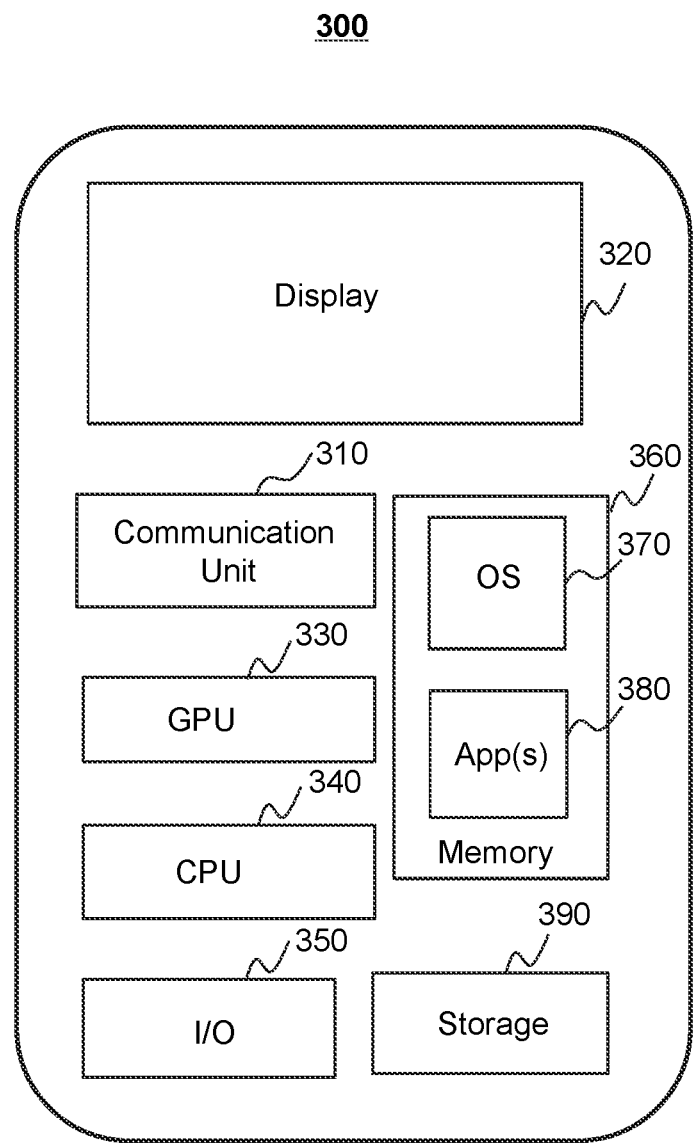
FIG. 3 is a schematic diagram illustrating exemplary hardware and/or software components of an exemplary mobile device on which the terminal may be implemented according to some embodiments of the present disclosure.

The terminal(s) 130 may include a mobile device 131, a tablet computer 132, a laptop computer 133, or the like, or any combination thereof. In some embodiments, the mobile device 131 may include a smart home device, a wearable device, a smart mobile device, a virtual reality device, an augmented reality device, or the like, or any combination thereof. Merely by way of example, the terminal 130 may include a mobile device as illustrated in FIG. 3. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footwear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing device 140.

The processing device 140 may process data and/or information obtained from the scanner 110, the terminal 130, and/or the storage device 150. For example, the processing device 140 may obtain a plurality of first sets of magnetic resonance (MR) image data of an object generated based on a plurality of first sets of imaging sequences. As another example, the processing device 140 may obtain a motion curve of the object. As still another example, the processing device 140 may obtain positron emission tomography (PET) image data of the object. As still another example, the processing device 140 may generate one or more target motion fields based on the plurality of first sets of MR image data and the motion curve. As still another example, the processing device 140 may generate one or more corrected PET images by correcting, based on the one or more target motion fields, the PET image data.

In some embodiments, the processing device 140 may be a single server or a server group. The server group may be centralized or distributed. In some embodiments, the processing device 140 may be local or remote. For example, the processing device 140 may access information and/or data stored in the scanner 110, the terminal 130, and/or the storage device 150 via the network 120. As another example, the processing device 140 may be directly connected to the scanner 110, the terminal 130 and/or the storage device 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2. In some embodiments, the processing device 140 may include a central processing unit (CPU). The CPU may include a single-core CPU, a Dual-core CPU, a Quad-core CPU, a Hex-core CPU, an Octa-core CPU, or the like, or any combination thereof.

The storage device 150 may store data, instructions, and/or any other information. In some embodiments, the storage device 150 may store data obtained from the scanner 110, the terminal 130 and/or the processing device 140. For example, the storage device 150 may store the plurality of first sets of magnetic resonance (MR) image data of the object generated based on the plurality of first sets of imaging sequences obtained from the scanner 110. As another example, the storage device 150 may store the one or more target motion fields generated by the processing device 140. In some embodiments, the storage device 150 may store data and/or instructions that the processing device 140 may execute or use to perform exemplary methods described in the present disclosure. For example, the storage device 150 may store instructions that the processing device 140 may execute or use to obtain the motion curve of the object. As another example, the storage device 150 may store instructions that the processing device 140 may execute or use to obtain the positron emission tomography (PET) image data of the object. As still another example, the storage device 150 may store instructions that the processing device 140 may execute or use to generate the one or more corrected PET images based on the one or more target motion fields and the PET image data.

In some embodiments, the storage device 150 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components of the image processing system 100 (e.g., the processing device 140, the terminal 130). One or more components of the image processing system 100 may access the data or instructions stored in the storage device 150 via the network 120. In some embodiments, the storage device 150 may be directly connected to or communicate with one or more other components of the image processing system 100 (e.g., the processing device 140, the terminal 130). In some embodiments, the storage device 150 may be part of the processing device 140.

FIG. 2 is a schematic diagram illustrating exemplary hardware and/or software components of an exemplary computing device on which the processing device 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may obtain a plurality of first sets of magnetic resonance (MR) image data of an object generated based on a plurality of first sets of imaging sequences. As another example, the processor 210 may obtain a motion curve of the object. As a further example, the processor 210 may obtain positron emission tomography (PET) image data of the object. As still a further example, the processor 210 may generate one or more target motion fields corresponding based on the plurality of first sets of MR image data and the motion curve. As still a further example, the processor 210 may generate one or more corrected PET images based on the one or more target motion fields and the PET image data. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both operations A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the scanner 110, the terminal 130, the storage device 150, and/or any other component of the image processing system 100. In some embodiments, the storage 220 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store an image processing program for generating one or more target motion fields. As another example, the storage 220 may store an image processing program for correcting image data (e.g., PET image data, MRI image data).

The I/O 230 may input and/or output signals, data, information, etc. In some embodiments, the I/O 230 may enable user interaction with the processing device 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing device 140 and the scanner 110, the terminal 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating exemplary hardware and/or software components of an exemplary mobile device 300 on which the terminal 130 may be implemented according to some embodiments of the present disclosure. As illustrated in FIG. 3, the mobile device 300 may include a communication unit 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system (OS) 370 (e.g., iOS™, Android™, Windows Phone™, etc.) and one or more applications (App(s)) 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the image processing system 100 via the network 120. In some embodiments, a user may input parameters to the image processing system 100, via the mobile device 300.

In order to implement various modules, units and their functions described above, a computer hardware platform may be used as hardware platforms of one or more elements (e.g., the processing device 140 and/or other components of the image processing system 100 described in FIG. 1). Since these hardware elements, operating systems and program languages are common; it may be assumed that persons skilled in the art may be familiar with these techniques and they may be able to provide information needed in the image processing operations according to the techniques described in the present disclosure. A computer with the user interface may be used as a personal computer (PC), or other types of workstations or terminal devices. After being properly programmed, a computer with the user interface may be used as a server. It may be considered that those skilled in the art may also be familiar with such structures, programs, or general operations of this type of computing device.

Figure 4:
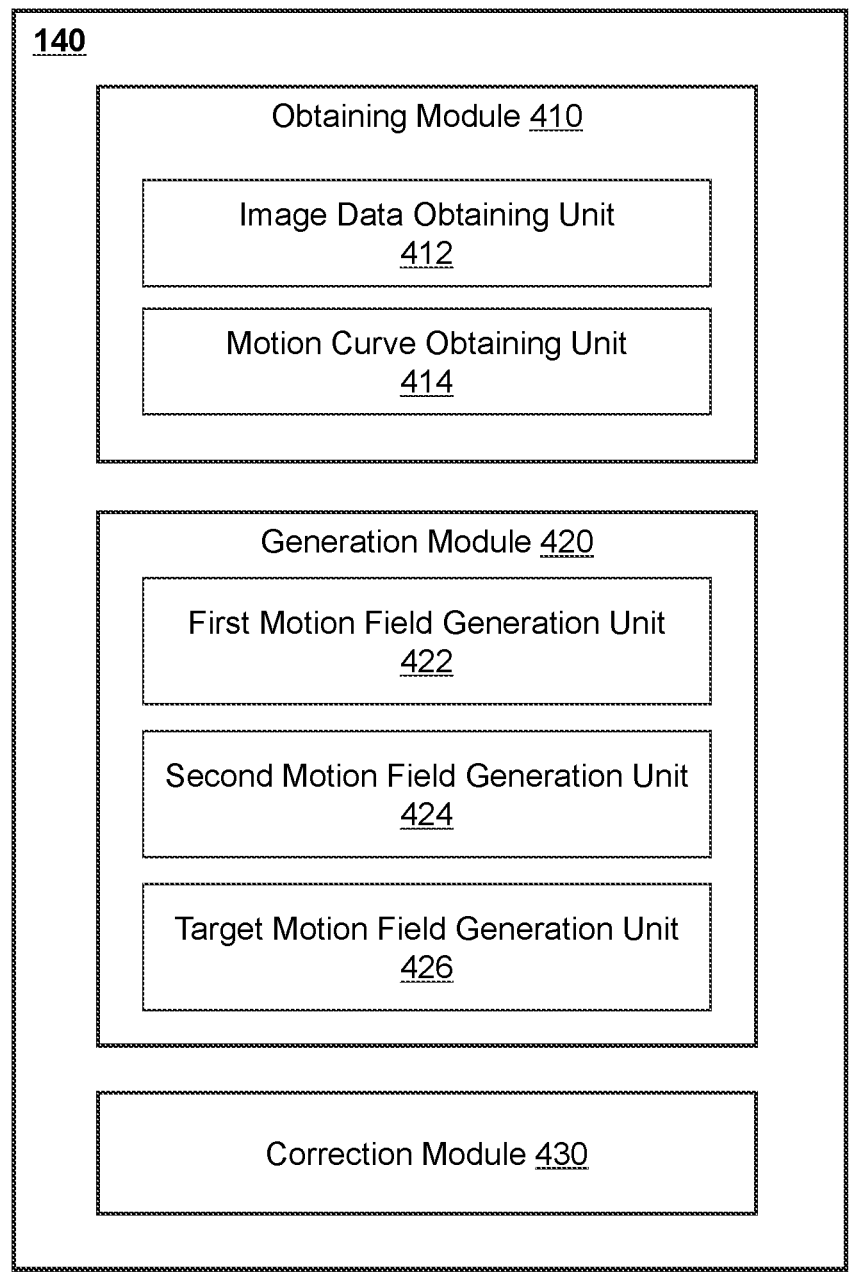
FIG. 4 is a block diagram illustrating an exemplary processing device according to some embodiments of the present disclosure.

FIG. 4 is a block diagram illustrating an exemplary processing device according to some embodiments of the present disclosure. As shown in FIG. 4, the processing device 140 may include an obtaining module 410, a generation module 420, and a correction module 430.

In some embodiments, the obtaining module 410 may be configured to obtain image data, a motion curve, or the like, or a combination thereof. In some embodiments, the obtaining module 410 may include an image data obtaining unit 412 and a motion curve obtaining unit 414. In some embodiments, the image data obtaining unit 412 may obtain a plurality of first sets of magnetic resonance (MR) image data of an object. In some embodiments, the image data obtaining unit 412 may obtain positron emission tomography (PET) image data of an object generated in a scanning time period. The PET image data may include PET raw data or data corresponding to one or more PET images reconstructed based on the PET raw data. In some embodiments, the image data obtaining unit 412 may obtain a plurality of second sets of MR image data of the object. In some embodiments, the motion curve obtaining unit 414 may obtain a motion curve of the object. More descriptions of the image data obtaining unit 412 and the motion curve obtaining unit 414 may be found elsewhere in the present disclosure (e.g., FIG. 5 and descriptions thereof).

In some embodiments, the generation module 420 may be configured to generate one or more motion fields. In some embodiments, the generation module 420 may include a first motion field generation unit 422, a second motion field generation unit 424, and a target motion field generation unit 426.

In some embodiments, the first motion field generation unit 422 may determine a plurality of respiratory phases of a respiratory motion of the object. In some embodiments, the first motion field generation unit 422 may determine a plurality of pieces of MR image data corresponding to the plurality of respiratory phases. In some embodiments, the first motion field generation unit 422 may reconstruct a plurality of images corresponding to the plurality of respiratory phases based on the plurality of pieces of MR image data. In some embodiments, the first motion field generation unit 422 may generate at least one first set of motion fields based on the plurality of images corresponding to the plurality of respiratory phases. In some embodiments, the first motion field generation unit 422 may determine a plurality of first sets of time intervals in which a plurality of first sets of MR image data are generated. In some embodiments, the first motion field generation unit 422 may determine at least one portion of the respiratory motion curve corresponding to the plurality of first sets of time intervals. In some embodiments, the first motion field generation unit 422 may determine a plurality of respiratory phases of the respiratory motion of the object based on the at least one portion of the respiratory motion curve.

In some embodiments, the second motion field generation unit 424 may determine a plurality of second sets of time intervals. In some embodiments, the second motion field generation unit 424 may obtain a plurality of second sets of motion fields based on the plurality of first sets of motion fields. In some embodiments, the second motion field generation unit 424 may obtain the second sets of motion fields by generating, based on the plurality of first sets of motion fields, at least one second set of motion fields corresponding to each second set of time intervals of the plurality of second sets of time intervals.

In some embodiments, the target motion field generation unit 426 may generate one or more target motion fields corresponding to the scanning time period based on the plurality of first sets of MR image data and the motion curve. In some embodiments, the target motion field generation unit 426 may generate one or more target motion fields based on the plurality of first sets of motion fields. In some embodiments, the target motion field generation unit 426 may generate at least a portion of the target motion fields by designating the first sets of motion fields as target motion fields. In some embodiments, the target motion field generation unit 426 may generate at least a portion of the target motion fields by duplicating the first sets of motion fields. In some embodiments, the target motion field generation unit 426 may generate at least a portion of the target motion fields by fitting the first sets of motion fields. In some embodiments, the target motion field generation unit 426 may generate the one or more target motion fields based on the plurality of first sets of motion fields and the plurality of second sets of motion fields. In some embodiments, the target motion field generation unit 426 may designate the plurality of first sets of motion fields and the plurality of second sets of motion fields as the one or more target motion fields.

In some embodiments, the correction module 430 may correct the PET image data and/or generate one or more corrected PET images based on the target motion fields and the PET image data. In some embodiments, the correction module 430 may generate the corrected PET images by correcting, based on the one or more target motion fields, the PET image data. In some embodiments, the correction module 430 may correct the second sets of MR image data and/or generate one or more corrected MR images based on the target motion fields and the second sets of MR image data.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 140 may further include a storage module (not shown in FIG. 4). The storage module may be configured to store data (e.g., the MR image data, the PET image data, the motion curve, the one or more target motion fields, the one or more corrected PET images, etc.) obtained and/or generated during any process performed by any component of the processing device 140. As another example, each of components of the processing device 140 may include a storage device. Additionally or alternatively, the components of the processing device 140 may share a storage device.

Figure 5:
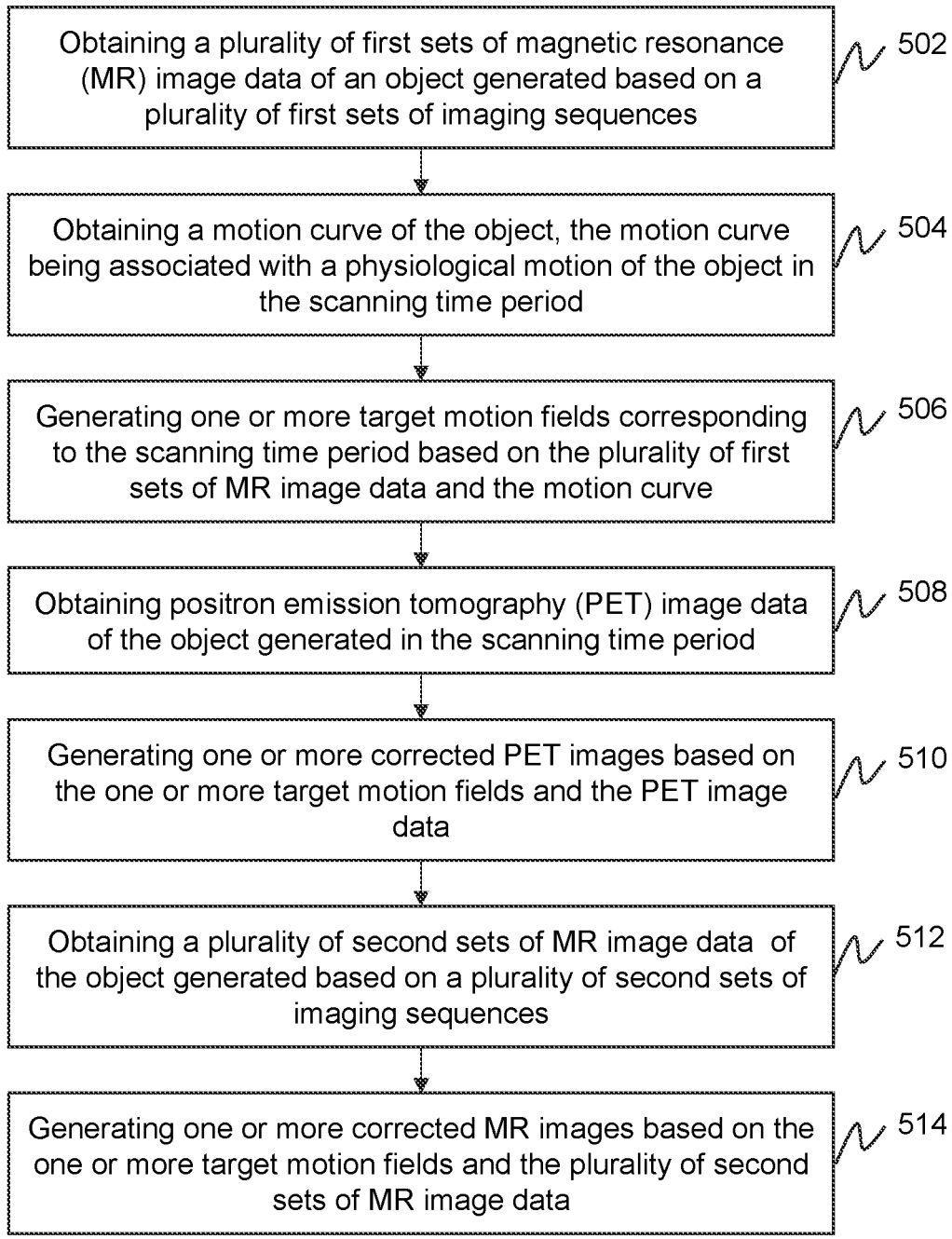
FIG. 5 is a flowchart illustrating an exemplary process for image processing according to some embodiments of the present disclosure.

FIG. 5 is a flowchart illustrating an exemplary process for image processing according to some embodiments of the present disclosure. In some embodiments, process 500 may be executed by the image processing system 100. For example, the process 500 may be implemented as a set of instructions (e.g., an application) stored in one or more storage devices (e.g., the storage device 150, the storage 220, and/or the storage 390) and invoked and/or executed by the processing device 140 (implemented on, for example, the processor 210 of the computing device 200, and the CPU 340 of the mobile device 300). The operations of the process 500 presented below are intended to be illustrative. In some embodiments, the process 500 may be accomplished with one or more additional operations not described, and/or without one or more of the operations discussed. Additionally, the order in which the operations of the process 500 as illustrated in FIG. 5 and described below is not intended to be limiting.

Figure 9:
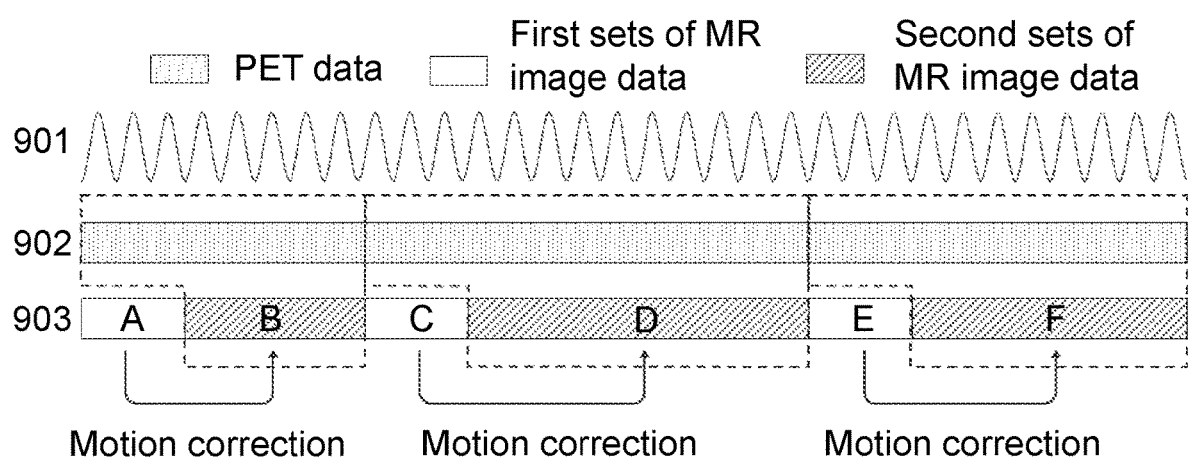
FIG. 9 is a schematic diagram illustrating an exemplary process for generating target motion fields and correcting image data based on the target motion fields according to some embodiments of the present disclosure.

In 502, the processing device 140 (e.g., the obtaining module 410, or the image data obtaining unit 412) may obtain a plurality of first sets of magnetic resonance (MR) image data of an object. In some embodiments, the first sets of MR image data may be obtained from the scanner 110. Alternatively or additionally, the first sets of MR image data may be obtained from the storage device 150 or an external data source. In some embodiments, a (or each) first set of MR image data may be used to reconstruct one or more MR images. Accordingly, the plurality of first sets of MR image data may be used to reconstruct a plurality of MR images. As shown in FIG. 9, the plurality of first sets of MR image data (e.g., the MR image data represented by the regions A, C, and/or E of the band 903) may be obtained.

In some embodiments, the plurality of first sets of MR image data may be generated based on a plurality of first sets of imaging sequences. A first set of MR image data may refer to image data generated based on a first set of imaging sequences. An imaging sequence may refer to or include a setting of one or more pulse sequences and/or one or more pulsed field gradients. The imaging sequence(s) may be used to scan the object and/or generate MR image data. The imaging sequence(s) may include or be associated with one or more parameters (e.g., a radio-frequency (RF) pulse, a gradient field, data acquisition time, etc.) and an arrangement thereof in sequence(s). Exemplary imaging sequences may include a free inductive decay (FID) sequence, a spin echo (SE) sequence, an inversion recovery (IR) sequence, a gradient echo (GRE) sequence, an echo planar imaging (EPI), or the like, or a combination thereof. In some embodiments, the imaging sequence(s) may be determined according to a scanning protocol. The scanning protocol may include imaging sequence(s) and scanning parameter(s). In some embodiments, the scanning protocol may be obtained from the storage device 150 or an external data source. In some embodiments, the scanning protocol may be provided by a user (e.g., a doctor, a technician, a physician, an engineer, etc.). In some embodiments, the scanning protocol may be generated automatically, for example, according to a machine learning model.

A first set of imaging sequences may be a special sequence used to scan the object and/or obtain motion field information associated with the object. In some embodiments, the first set of imaging sequences may be different from a general sequence that is used to scan the object and/or obtain image data of the object. Exemplary first sets of imaging sequences may include a multi-cycle radial imaging sequence, a spiral imaging sequence, a random imaging sequence, a radial imaging sequence with a golden-angle scheme, or the like, or a combination thereof. In some embodiments, the first set of imaging sequences may last a relatively short time period, for example, one or more (e.g., two or three) respiratory cycles. Accordingly, a first set of MR image data generated based on the first set of imaging sequences may correspond to image data generated in the one or more respiratory cycles. In some embodiments, the plurality of first sets of imaging sequences may be separated in a scanning time period. As used herein, the scanning time period may refer to or include an entire scanning time period in which the first sets of MR image data (as illustrated in 502), the PET image data (as illustrated in 508), and/or the second sets of MR image data (as illustrated in 512) are generated. In some embodiments, each first set of imaging sequences may be separated from another first set of imaging sequences in time.

In 504, the processing device 140 (e.g., the obtaining module 410, or the motion curve obtaining unit 414) may obtain a motion curve of the object. In some embodiments, the motion curve may be obtained from the scanner 110. In some embodiments, the motion curve may be obtained from a motion detection device associated with or external to the image processing system 100. Alternatively or additionally, the motion curve may be obtained from the storage device 150 or an external data source.

The motion curve may express a physiological motion of the object in the scanning time period. As shown in FIG. 9, the waveform 901 may indicate an exemplary motion curve of an object collected during a scanning time period. In some embodiments, the scanning time period may be relatively long (e.g., the scanning time period may include multiple respiratory cycles or phases), and it may be difficult for the object to keep in a static state, or maintain a same physiological motion state during the scanning time period. Data associated with the multiple respiratory cycles or phases may be recorded during the scanning time period to obtain the motion curve. In some embodiments, the processing device 140 (e.g., the obtaining module 410) may obtain the motion curve of the object when the first sets of MR image data are generated based on the plurality of first sets of imaging sequences. In some embodiments, the generation of at least a portion of the motion curve and the generation of the first sets of MR image data may be performed simultaneously or synchronously.

In some embodiments, the motion curve may include a respiratory motion curve, a cardiac motion curve, or the like, or any combination thereof. In some embodiments, the motion curve may be obtained or generated by recording physiological motion data (e.g., using a motion detection device) during the scanning time period. Exemplary motion detection devices may include an abdominal band, a camera, a contactless sensing device, a vital sign data acquisition device, or the like, or a combination thereof. In some embodiments, the motion detection device may be integrated into the image processing system 100 (e.g., the scanner 110). In some embodiments, the motion detection device may be external to the image processing system 100 (e.g., the motion detection device may not be integrated into the scanner 110). For example, an abdominal band may be worn (e.g., before the object is scanned) on the abdomen of the object to collect respiratory signals during the scanning time period, and then the collected respiratory signals may be processed to obtain the respiratory motion curve. As another example, the scanner 110 (e.g., an MRI scanner) may be equipped with a camera that may be used to capture images of the object during the scanning time period, and the images may be processed (e.g., data of region(s) of interest (e.g., a chest, an abdomen, etc.) may be extracted from the images, and/or the extracted data may be further processed) to obtain the respiratory motion curve. As a further example, one or more contactless sensing devices (e.g., a radar, a coil, etc.) may be disposed in the scanner 110 to collect respiratory signals of the object. As still a further example, a vital sign data acquisition device may be disposed in the scanner 110 to generate or obtain a physiological motion curve. Exemplary vital sign data acquisition devices may include a vital sign data acquisition device based on an electromagnetic echo signal, a vital sign data acquisition device based on an electrocardiograph (ECG) signal, a vital sign data acquisition device based on a photoelectric signal, a vital signs data acquisition device based on a pressure oscillation signal, or the like, or any combination thereof.

In some embodiments, if a PET-MRI scanner is used, the motion curve may be obtained by processing PET data generated during the scanning time period. In some embodiments, the respiratory motion curve may be obtained or generated by extracting data relating to the physiological motion of the object based on imaging data (e.g., raw data, image data) collected by the MRI scanner, and processing the data. It should be noted that the obtaining of the motion curve illustrated above is merely provided for the purposes of illustration, and not intended to limit the scope of the present disclosure.

In 506, the processing device 140 (e.g., the generation module 420, or the target motion field generation unit 426) may generate one or more target motion fields corresponding to the scanning time period based on the plurality of first sets of MR image data and the motion curve.

A motion field may refer to a function that maps or registers two or more images (e.g., images generated in different physiological motion states (e.g., different respiratory cycles or phases) of the object). For example, a first image generated in a physiological motion state SA may be registered, based on a motion field, with a second image generated in a physiological motion state SB. Alternatively or additionally, by using the motion field to register the first image with the second image, a (or each) first pixel or voxel in the first image may be moved to a position of a corresponding second pixel or voxel in the second image, in which the first pixel or voxel and the corresponding second pixel or voxel may represent a same portion of the object. In some embodiments, if the first image is processed based on the motion field, the processed first image may be substantially consistent with the second image.

The target motion fields may refer to motion fields corresponding to the scanning time period. In some embodiments, a (or each) target motion field may correspond to a specific time point or time period within the scanning time period, or a (or each) target motion field may correspond to a specific respiratory cycle or phase (or a specific respiratory phase of a specific respiratory cycle) within the scanning time period, and accordingly, the scanning time period may correspond to multiple target motion fields. The target motion fields may be further used to correct image data (e.g., MR image data, PET image data) and/or remove or eliminate motion artifacts in images corresponding to the image data. In some embodiments, the one or more target motion fields corresponding to the scanning time period may be generated based on the plurality of first sets of MR image data and the motion curve. More descriptions of the generation of the target motion fields may be found elsewhere in the present disclosure (e.g., FIGS. 6-8 and descriptions thereof).

In 508, the processing device 140 (e.g., the obtaining module 410, or the image data obtaining unit 412) may obtain positron emission tomography (PET) image data of the object generated in the scanning time period. As shown in FIG. 9, the band 902 may indicate PET image data generated in the scanning time period. The PET image data may include PET raw data or data corresponding to one or more PET images reconstructed based on the PET raw data. In some embodiments, the generation of at least a portion of the PET image data may be simultaneous or synchronous to the generation of the plurality of first sets of MR image data. That is, an image reconstructed by a first set of MR image data may correspond to an image reconstructed based on at least a portion of the PET image data. In some embodiments, the generation of the motion curve and the generation of the PET image data may be performed simultaneously or synchronously. For example, the scanner 110 may be a PET-MRI scanner, and during PET scanning (or during the generation of the PET image data), the MR scanning may be performed (or the first sets of MR image data may be generated) simultaneously or synchronously, and the motion signal collection may also be performed simultaneously or synchronously.

In 510, the processing device 140 (e.g., the correction module 430) may correct the PET image data and/or generate one or more corrected PET images based on the target motion fields and the PET image data. In some embodiments, the processing 140 may generate the corrected PET images by correcting, based on the one or more target motion fields, the PET image data. According to operations 502 through 510, generally, the PET image data may be corrected based on the first sets of MR image data and the motion curve. As shown in FIG. 9, the PET image data (e.g., the PET image data represented by the band 902) may be corrected based on the plurality of first sets of MR image data (e.g., the MR image data represented by the regions A, C, and/or E of the band 903).

In some embodiments, a pre-reconstruction or a post-reconstruction operation may be performed to correct the PET image data. The pre-reconstruction operation may refer to a correction operation on the PET raw data followed by an image reconstruction operation on the corrected PET raw data. In some embodiments, after correcting the PET raw data based on the one or more target motion fields, the corrected PET raw data may be used for image reconstruction to obtain corrected PET images including no or reduced motion artifact(s). The post-reconstruction operation may refer to an image reconstruction operation on the PET raw data followed by a correction operation on the reconstructed PET images. In some embodiments, after the PET raw data are used for image reconstruction to obtain PET images, the PET images may be corrected, based on the one or more target motion fields, to obtain corrected PET images including no or reduced motion artifact(s). In some embodiments, a (or each) piece of PET raw data or a (or each) corresponding reconstructed PET image that is generated at a specific time point or time period may correspond to a target motion field with respect to the specific time point or time period. In some embodiments, the PET raw data or the reconstructed PET images may be multiplied by corresponding target motion fields to obtain corrected PET images.

In 512, the processing device 140 (e.g., the obtaining module 410, or the image data obtaining unit 412) may obtain a plurality of second sets of MR image data of the object. In some embodiments, the second sets of MR image data may be obtained from the scanner 110. Alternatively or additionally, the second sets of MR image data may be obtained from the storage device 150 or an external data source. In some embodiments, a (or each) second set of MR image data may be used to reconstruct one or more MR images. Accordingly, the plurality of second sets of MR image data may be used to reconstruct a plurality of MR images. As shown in FIG. 9, the plurality of second sets of MR image data (e.g., the MR image data represented by the regions B, D, and/or F of the band 903) may be obtained. The plurality of second sets of MR image data may include MR raw data or data corresponding to one or more MR images reconstructed based on the MR raw data.

In some embodiments, the plurality of second sets of MR image data may be generated based on a plurality of second sets of imaging sequences. A second set of MR image data may refer to image data generated based on a second set of imaging sequences. In some embodiments, a second set of imaging sequences may be a general set of sequences that is used to scan the object and/or obtain image data of the object. The second sets of imaging sequences may be different from the first sets of imaging sequences. Exemplary second sets of imaging sequences may include a free inductive decay (FID) sequence, a spin echo (SE) sequence, an inversion recovery (IR) sequence, a gradient echo (GRE) sequence, an echo planar imaging (EPI) sequence, or the like, or a combination thereof. In some embodiments, as described in 502, the first set of imaging sequences may last a relatively short time period, for example, one or more (e.g., two or three) respiratory cycles. In some embodiments, the second set of imaging sequences may last a relatively long time period (e.g., one or more minutes) with respect to the first set of imaging sequences. Accordingly, a second set of MR image data generated based on the second set of imaging sequences may correspond to image data generated in the relatively long time period. In some embodiments, the second sets of MR image data may include clinical information of the object and/or be used to reconstruct clinical images of the object, while the first sets of MR image data may be used to obtain motion field information associated with the object.

In some embodiments, as described in 502, the plurality of first sets of imaging sequences may be separated in the entire scanning time period. In some embodiments, the plurality of second sets of imaging sequences may be interleaved with the plurality of first sets of imaging sequences. For example, two adjacent second sets of imaging sequences may be spaced apart by a first set of imaging sequences, or two adjacent first sets of imaging sequences may be spaced apart by one or more second sets of imaging sequences. In some embodiments, the entire scanning time period may include a first plurality of time periods corresponding to the first sets of imaging sequences and a second plurality of time periods corresponding to the second sets of imaging sequences. In some embodiments, the distribution of the first sets of imaging sequences and/or the second sets of imaging sequences through the entire scanning time period may be ununiform. In some embodiments, the plurality of first sets of imaging sequences may be sparsely interspersed between the plurality of second sets of imaging sequences. For example, each two adjacent first sets of imaging sequences may be spaced apart by one or more second sets of imaging sequences. Accordingly, the second plurality of time periods corresponding to the second sets of imaging sequences may be longer than the first plurality of time periods corresponding to the first sets of imaging sequences. Further, the number or count of the second plurality of time periods corresponding to the second sets of imaging sequences may be larger than the number or count of the first plurality of time periods corresponding to the first sets of imaging sequences. For example, if the entire scanning time period lasts 20 minutes, the first plurality of time periods corresponding to the first sets of imaging sequences may be 1 minute, while the second plurality of time periods corresponding to the second sets of imaging sequences may be 19 minutes. In some embodiments, within the entire scanning time period, a time delay may be present between two successive sets of imaging sequences (e.g., a first set of imaging sequences and a successive second set of imaging sequences, a second set of imaging sequences and a successive first set of imaging sequences, two successive second sets of imaging sequences, or the like). In some embodiments, within the entire scanning time period, no time delay may be present between two successive sets of imaging sequences.

In some embodiments, the plurality of first sets of imaging sequences may be only interspersed between a portion of the second sets of imaging sequences (e.g., the second sets of imaging sequences used to scan an abdomen, a breast, a chest, or the like). Therefore, the scanner 110 may scan the object in time and efficiently, and the processing device 140 (e.g., the obtaining module 410) may efficiently obtain the plurality of first sets of MR image data of the object generated based on the plurality of first sets of imaging sequences and the plurality of second sets of MR image data of the object generated based on the plurality of second sets of imaging sequences. Through the sparsely interspersing of the plurality of first sets of imaging sequences, relatively small amount of first sets of MR image data of the object may be obtained to generate the target motion fields, and sufficient second sets of MR image data of the object may be obtained to reconstruct diagnosis images of the object, thereby ensuring image qualities and improving image acquisition efficiencies.

In some embodiments, the generation of at least a portion of the PET image data (illustrated in 508) may be simultaneous or synchronous to the generation of the plurality of second sets of MR image data. That is, an image reconstructed by a second set of MR image data may correspond to an image reconstructed based on at least a portion of the PET image data. In some embodiments, the generation or collection of at least a portion of the motion curve (illustrated in 504) may be simultaneous or synchronous to the generation of the plurality of second sets of MR image data.

In 514, the processing device 140 (e.g., the correction module 430) may correct the second sets of MR image data and/or generate one or more corrected MR images based on the target motion fields and the second sets of MR image data. In some embodiments, the one or more corrected MR images may be generated by correcting, based on the one or more target motion fields, the plurality of second sets of MR image data. According to operations 502 through 514, generally, the second sets of MR image data may be corrected based on the first sets of MR image data and the motion curve. As shown in FIG. 9, the second sets of MR image data (e.g., the MR image data represented by the regions B, D, and/or F of the band 903) may be corrected based on the plurality of first sets of MR image data (e.g., the MR image data represented by the regions A, C, and/or E of the band 903).

In some embodiments, a pre-reconstruction or a post-reconstruction operation may be performed to correct the second sets of MR image data. The pre-reconstruction operation may refer to a correction operation on the MR raw data followed by an image reconstruction operation on the corrected MR raw data. In some embodiments, after correcting the MR raw data based on the one or more target motion fields, the corrected MR raw data may be used for image reconstruction to obtain corrected MR images including no or reduced motion artifact(s). The post-reconstruction operation may refer to an image reconstruction operation on the MR raw data followed by a correction operation on the reconstructed MR images. In some embodiments, after the MR raw data are used for image reconstruction to obtain MR images, the MR images may be corrected, based on the one or more target motion fields, to obtain corrected MR images including no or reduced motion artifact(s). In some embodiments, a (or each) piece of MR raw data or a (or each) corresponding reconstructed MR image that is generated at a specific time point or time period may correspond to a target motion field with respect to the specific time point or time period. In some embodiments, the MR raw data or the reconstructed MR images may be multiplied by corresponding target motion fields to obtain corrected MR images.

Referring to FIG. 9, FIG. 9 is a schematic diagram illustrating an exemplary process for generating target motion fields and correcting image data based on the target motion fields according to some embodiments of the present disclosure. The waveform 901 may indicate an exemplary motion curve of an object collected during a scanning time period. The band 902 may indicate PET image data generated in the scanning time period. The band 903 may indicate MR image data generated in the scanning time period. The regions A, C, and/or E of the band 903 may represent the first sets of MR image data generated based on the first sets of imaging sequences, while the regions B, D, and/or F of the band 903 may represent the second sets of MR image data generated based on the second sets of imaging sequences, in which the first sets of imaging sequences may be sparsely interspersed between the second sets of imaging sequences. The first sets of MR image data (represented by the regions A, C, and/or E of the band 903) and the motion curve of the object (represented by the waveform 901) may be used to generate target motion fields, and the target motion fields may be further used to correct the second sets of MR image data (represented by the regions B, D, and/or F of the band 903) and/or the PET image data (represented by the band 902) to generate corrected MR images and/or corrected PET images including no or reduced motion artifact(s). It should be noted that in some embodiments, the use of the second sets of imaging sequences is not necessary. That is, within the entire scanning time period, only first sets of imaging sequences may be used sparsely, and accordingly, only first sets of MR image data may be generated, while the second sets of imaging sequences may not be used, and the second sets of MR image data may not be generated. In such cases, the regions B, D, and/or F of the band 903 may be blank, and the first sets of MR image data may only be used to correct the PET image data. In some embodiments, the first sets of MR image data (or the second sets of MR image data), and the PET image data may be collected simultaneously or synchronously by a PET-MRI scanner. In some embodiments, the second sets of MR image data and the PET image data may be corrected as illustrated above, respectively. In some embodiments, the corrected MR images and the corrected PET images may be registered and/or fused to obtain multi-modality images to facilitate image analyses and/or disease diagnoses.

It should be noted that the above description of process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, operation 504 may be performed before or simultaneously with operation 502. As another example, operation 508 may be performed before or simultaneously with operations 502 and/or 504. As still another example, one or more of operations 508 through 514 may be omitted. As a further example, operations 502 and 512 may be performed alternately.

Figure 6:
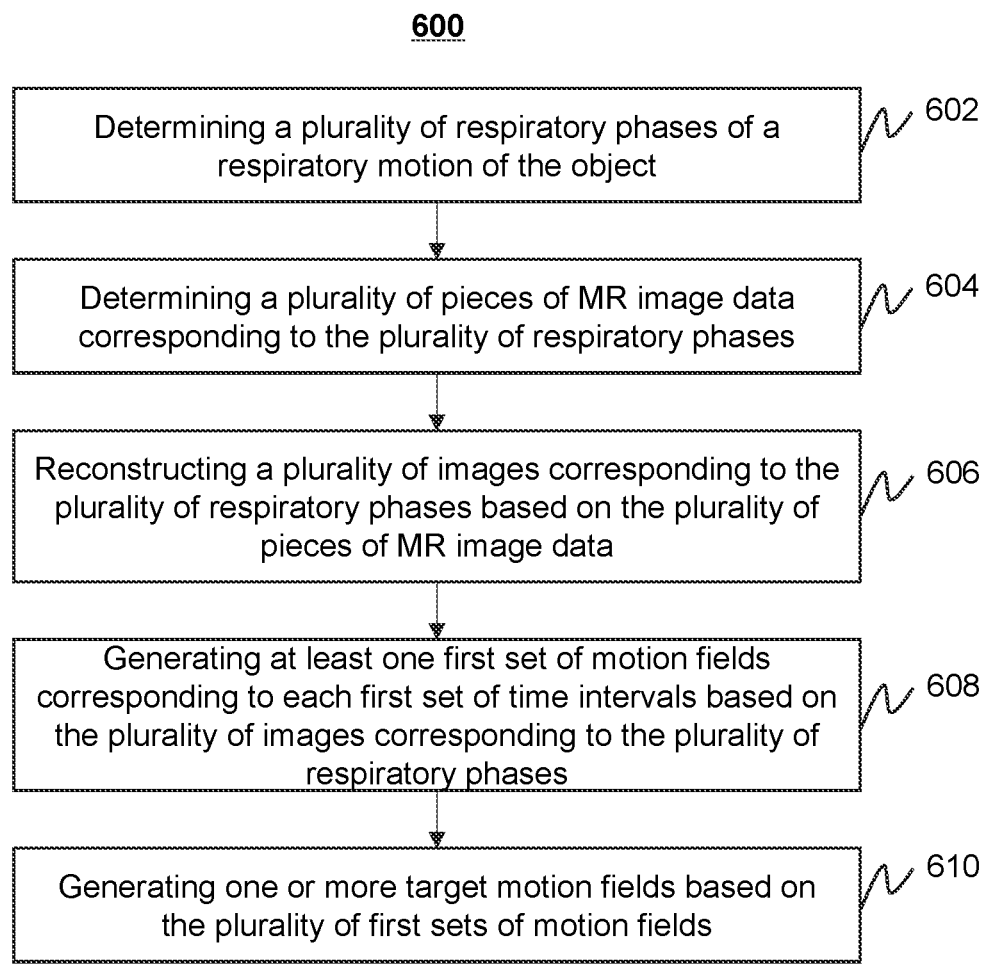
FIG. 6 is a flowchart illustrating an exemplary process for generating target motion fields according to some embodiments of the present disclosure.

FIG. 6 is a flowchart illustrating an exemplary process for generating target motion fields according to some embodiments of the present disclosure. In some embodiments, at least part of process 600 may be performed by the processing device 140 (implemented in, for example, the computing device 200 shown in FIG. 2). For example, the process 600 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting. In some embodiments, operation 506 illustrated in FIG. 5 may be performed according to the process 600.

In 602, the processing device 140 (e.g., the generation module 420, or the first motion field generation unit 422) may determine a plurality of respiratory phases of a respiratory motion of the object. In some embodiments, the respiratory motion of the object may include a plurality of respiratory cycles. A (or each) respiratory cycle may include one or more respiratory phases. A respiratory phase may correspond to or indicate a specific respiratory state of the object. Exemplary respiratory phases in a respiratory cycle may include an initial stage of inspiration, an end stage of inspiration, an initial stage of expiration, an end stage of expiration, etc. In some embodiments, different respiratory cycles may have the same respiratory phases. For example, a first respiratory cycle may include an initial stage of inspiration, an end stage of inspiration, an initial stage of expiration, and an end stage of expiration, and a second respiratory cycle may also include an initial stage of inspiration, an end stage of inspiration, an initial stage of expiration, and an end stage of expiration. It should be noted that the above exemplary respiratory phases are merely provided for the purposes of illustration, and not intended to limit the scope of the present disclosure. In some embodiments, the plurality of respiratory phases of the respiratory motion of the object may be determined based on at least one portion of a respiratory motion curve of the object. More descriptions of the determination of the plurality of respiratory phases of the respiratory motion of the object may be found elsewhere in the present disclosure (e.g., FIG. 7 and descriptions thereof).

In 604, the processing device 140 (e.g., the generation module 420, or the first motion field generation unit 422) may determine a plurality of pieces of MR image data corresponding to the plurality of respiratory phases. A (or each) piece of MR image data may correspond to a respiratory phase. In some embodiments, as illustrated in FIG. 5, a generation of at least a portion of the respiratory motion curve may be simultaneous or synchronous to a generation of the plurality of first sets of MR image data, each first set of MR image data generated based on a first set of imaging sequences may correspond to one or more respiratory cycles, and each respiratory cycle may include one or more respiratory phases. In some embodiments, the plurality of pieces of MR image data may be determined by determining, based on the plurality of first sets of MR image data and at least a portion of the respiratory motion curve, a piece of MR image data corresponding to each of the plurality of respiratory phases. Specifically, the plurality of first sets of MR image data may be divided into the plurality of pieces of MR image data corresponding to the plurality of respiratory phases, based on the plurality of first sets of MR image data and the plurality of respiratory phases. In some embodiments, a (or each) first set of MR image data may be divided into multiple pieces of MR image data corresponding to multiple respiratory phases. Merely by way of example, if a first set of imaging sequences corresponds to two respiratory cycles, each respiratory cycle includes four respiratory phases (i.e., the first set of imaging sequences corresponds to eight respiratory phases), then a first set of MR image data generated based on the first set of imaging sequences may correspond to eight respiratory phases, and the first set of MR image data may be divided into eight pieces of MR image data corresponding to the eight respiratory phases. In some embodiments, a (or each) respiratory phase may have a timestamp (e.g., a recorded time point or time period) correlative to the entire scanning time period, and the MR image data collected by the scanner 110 may also have timestamps (e.g., recorded time points or time periods) correlative to the entire scanning time period, and thus, the first set(s) of MR image data may be divided, based on the timestamp(s) of the respiratory phase(s) and the timestamp(s) of the first set(s) of MR image data, to obtain the piece(s) of MR image data.

In 606, the processing device 140 (e.g., the generation module 420, or the first motion field generation unit 422) may reconstruct a plurality of images corresponding to the plurality of respiratory phases based on the plurality of pieces of MR image data. The images may be reconstructed using one or more reconstruction algorithms. Exemplary reconstruction algorithms may include a rapid reconstruction, an algebraic reconstruction, an iteration reconstruction, a back projection reconstruction, or the like, or any combination thereof. Exemplary rapid reconstruction algorithms may include fast Fourier transform, a compressed sensing algorithm, a deep learning algorithm, or the like, or any combination thereof. In some embodiments, the plurality of reconstructed images corresponding to the plurality of respiratory phases may include no or reduced motion artifact(s). In some embodiments, motion correction may be performed before, during, or after image reconstruction to obtain images including no or reduced motion artifact(s). The motion correction may include pre-reconstruction, post-reconstruction, or the combination thereof. If pre-reconstruction is performed, raw data corresponding to the pieces of MR image data may be corrected and then reconstructed to obtain images including no or reduced motion artifact(s). If post-reconstruction is performed, raw data corresponding to the pieces of MR image data may be reconstructed to obtain images (including motion artifact(s)) and then be corrected to obtain images including no or reduced motion artifact(s). In some embodiments, a (or each) piece of MR image data corresponding to a respiratory phase may be used to reconstruct an image including no or reduced motion artifact(s). In some embodiments, two or more pieces of MR images data corresponding to a same respiratory phase in different respiratory cycles may be used to reconstruct an image including no or reduced motion artifact(s).

In 608, the processing device 140 (e.g., the generation module 420, or the first motion field generation unit 422) may generate at least one first set(s) of motion fields based on the plurality of images corresponding to the plurality of respiratory phases. A first set of motion fields may refer to a set of motion fields derived from the first set(s) of MR image data generated based on the first set(s) of imaging sequences. A motion field may refer to a function that maps or registers a first image corresponding to a respiratory phase A with a second image (also referred to as a reference image) corresponding to a respiratory phase B (e.g., a reference respiratory phase (e.g., a resting period of an end stage of expiration)). More descriptions of the motion field may be found elsewhere in the present disclosure (e.g., FIG. 5 and descriptions thereof). In some embodiments, a (or each) first set of motion fields may correspond to a respiratory phase. In some embodiments, one or more first sets of motion fields (or at least one first set of motion fields) may correspond to a first set of time intervals in which one first set of MR image data are generated. In some embodiments, a plurality of first sets of motion fields may be obtained by generating, based on the motion curve, at least one first set of motion fields corresponding to each first set of time intervals in which one first set of MR image data among the plurality of first sets of MR image data are generated. In some embodiments, a (or each) first set of motion fields may be generated by registering a corresponding reconstructed image with a reference image.

In some embodiments, an image corresponding to a specific respiratory phase of a specific respiratory cycle may be used as a reference image for all respiratory cycles. Merely by way of example, if a first set of time intervals includes two respiratory cycles (e.g., a first respiratory cycle, a second respiratory cycle), a respiratory cycle includes four respiratory phases (e.g., a first respiratory phase, a second respiratory phase, a third respiratory phase, and a fourth respiratory phase), eight images (e.g., a first image corresponding to the first respiratory phase of the first respiratory cycle, a second image corresponding to the second respiratory phase of the first respiratory cycle, a third image corresponding to the third respiratory phase of the first respiratory cycle, a fourth image corresponding to the fourth respiratory phase of the first respiratory cycle, a fifth image corresponding to the first respiratory phase of the second respiratory cycle, a sixth image corresponding to the second respiratory phase of the second respiratory cycle, a seventh image corresponding to the third respiratory phase of the second respiratory cycle, and an eighth image corresponding to the fourth respiratory phase of the second respiratory cycle) including no or reduced motion artifact(s) are reconstructed, and the first image corresponding to the first respiratory phase of the first respiratory cycle is used as the reference image for all respiratory cycles, then seven first sets of motion fields corresponding to the first sets of time intervals may be generated (e.g., a first set of motion fields M1 may be generated by registering the second image with the first image, a second set of motion fields M2 may be generated by registering the third image with the first image, a third motion field M3 may be generated by registering the fourth image with the first image, a fourth motion field M4 may be generated by registering the fifth image with the first image, a fifth motion field M5 may be generated by registering the sixth image with the first image, a sixth motion field M6 may be generated by registering the seventh image with the first image, a seventh motion field M7 may be generated by registering the eighth image with the first image).

In some embodiments, an image corresponding to a specific respiratory phase of a current respiratory cycle may be used as a reference image for the current respiratory cycles. Merely by way of example, as illustrated above, if the first image corresponding to the first respiratory phase of the first respiratory cycle is used as the reference image for the first respiratory cycle, and the fifth image corresponding to the first respiratory phase of the second respiratory cycle is used as the reference image for the second respiratory cycle, then six first sets of motion fields corresponding to the first set of time intervals may be generated (e.g., a first set of motion fields M1 may be generated by registering the second image with the first image, a second set of motion fields M2 may be generated by registering the third image with the first image, a third set of motion fields M3 may be generated by registering the fourth image with the first image, a fourth set of motion fields M4 may be generated by registering the sixth image with the fifth image, a fifth set of motion fields M5 may be generated by registering the seventh image with the fifth image, a sixth set of motion fields M6 may be generated by registering the eighth image with the fifth image).

In 610, the processing device 140 (e.g., the generation module 420, or the target motion field generation unit 426) may generate one or more target motion fields based on the plurality of first sets of motion fields. In some embodiments, at least a portion of the target motion fields may be generated by designating the first sets of motion fields as target motion fields. In some embodiments, at least a portion of the target motion fields may be generated by duplicating the first sets of motion fields. In some embodiments, at least a portion of the target motion fields may be generated by fitting the first sets of motion fields. More descriptions of the generation of the target motion fields may be found elsewhere in the present disclosure (e.g., FIG. 8 and descriptions thereof).

It should be noted that the above description of process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, operations 602 and 604 may be integrated into a single operation.

Figure 7:
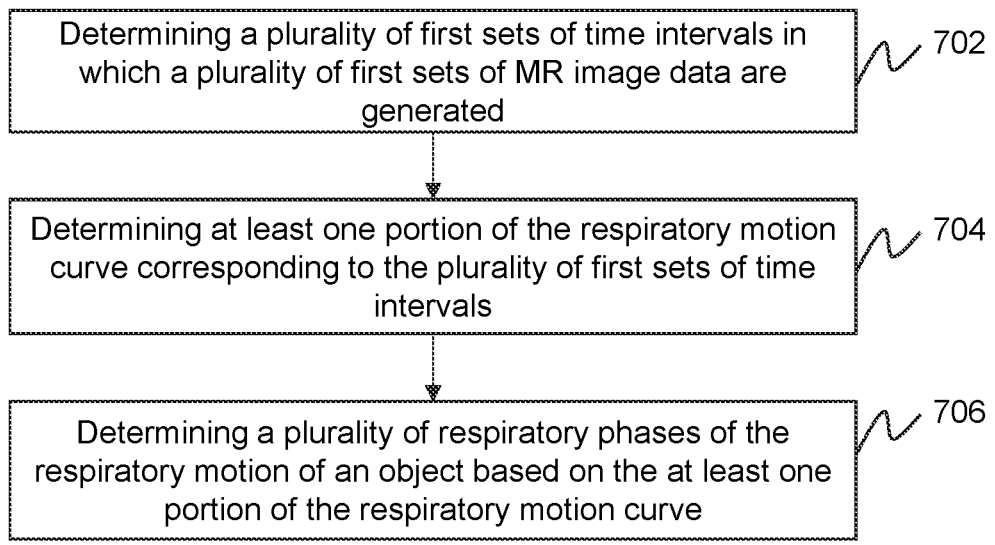
FIG. 7 is a flowchart illustrating an exemplary process for determining a plurality of respiratory phases of a respiratory motion of an object according to some embodiments of the present disclosure.

FIG. 7 is a flowchart illustrating an exemplary process for determining a plurality of respiratory phases of a respiratory motion of an object according to some embodiments of the present disclosure. In some embodiments, at least part of process 700 may be performed by the processing device 140 (implemented in, for example, the computing device 200 shown in FIG. 2). For example, the process 700 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 700 may be accomplished with one or more additional operations not described, and/or without one or more of the operations discussed. Additionally, the order in which the operations of the process 800 as illustrated in FIG. 7 and described below is not intended to be limiting. In some embodiments, operation 602 illustrated in FIG. 6 may be performed according to the process 700.

In 702, the processing device 140 (e.g., the generation module 420, or the first motion field generation unit 422) may determine a plurality of first sets of time intervals in which a plurality of first sets of MR image data are generated. A first set of time intervals may refer to a time period in which one first set of MR image data are generated. The first set of time intervals may include a start time point, a length, and/or an end time point. The first set of time intervals may correspond to a time period in which one of the plurality of first sets of imaging sequences is used to generate a first set of MR image data. In some embodiments, a first time period in which a (or each) first set of imaging sequences is used may be recorded during scanning, and accordingly, a second time period in which a corresponding first set of MR image data are generated based on the first set of imaging sequences may be recorded during scanning. In some embodiments, the first time period and the second time period may be the same. For example, a start time point, a length, and/or an end time point of the first time period may be the same as those of the second time period. Thus, a first set of time intervals in which a first set of MR image data is generated may be determined based on the recorded time period(s). Accordingly, the plurality of first sets of time intervals in which the plurality of first sets of MR image data are generated may be determined.

In 704, the processing device 140 (e.g., the generation module 420, or the first motion field generation unit 422) may determine at least one portion of the respiratory motion curve corresponding to the plurality of first sets of time intervals. As illustrated in FIG. 5, in some embodiments, a generation of at least a portion of the respiratory motion curve may be simultaneous or synchronous to a generation of the plurality of first sets of MR image data, and thus, a time frame of the respiratory motion curve may be associated with or correlated to that of the plurality of first sets of MR image data. That is, the time frame of the respiratory motion curve may be associated with or correlated to the plurality of first sets of time intervals. Thus, at least one portion of the respiratory motion curve corresponding to the plurality of first sets of time intervals may be determined. For example, if a first set of time intervals $T_a$ is from time point $t_0$ to time point $t_1$, then a segment of the respiratory motion curve corresponding to the time interval $t_0$-$t_1$ may be retrieved from the respiratory motion curve. Similarly, a plurality of segments of the respiratory motion curve corresponding to the plurality of first sets of time intervals may be determined. The time frame of the respiratory motion curve may include a plurality of timestamps.

In 706, the processing device 140 (e.g., the generation module 420, or the first motion field generation unit 422) may determine a plurality of respiratory phases of the respiratory motion of the object based on the at least one portion of the respiratory motion curve. In some embodiments, as illustrated in FIGS. 5-6, a first set of time intervals may include one or more respiratory cycles, and each respiratory cycle may include one or more respiratory phases. As illustrated in 704, a segment of the respiratory motion curve may correspond to a first set of time intervals, and thus, the segment of the respiratory motion curve may correspond to one or more respiratory phases. In some embodiments, the respiratory phases corresponding to a first set of time intervals may be determined based on a waveform of the segment of the respiratory motion curve corresponding to the first set of time intervals. For example, if a first set of time intervals includes two respiratory cycles, and each respiratory cycle includes four respiratory phases (e.g., a first respiratory phase, a second respiratory phase, a third respiratory phase, and a fourth respiratory phase), then the first respiratory phase of the first respiratory cycle, the second respiratory phase of the first respiratory cycle, the third respiratory phase of the first respiratory cycle, the fourth respiratory phase of the first respiratory cycle, the first respiratory phase of the second respiratory cycle, the second respiratory phase of the second respiratory cycle, the third respiratory phase of the second respiratory cycle, and the fourth respiratory phase of the second respiratory cycle may be directly identified from the waveform of the segment of the respiratory motion curve corresponding to the first set of time intervals. In some embodiments, a start time point, a length, and/or an end time point of each respiratory phase may also be identified from the waveform of the segment of the respiratory motion curve corresponding to the first set of time intervals.

It should be noted that the above description of process 700 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, operations 702 and 704 may be integrated into a single operation.

Figure 8:
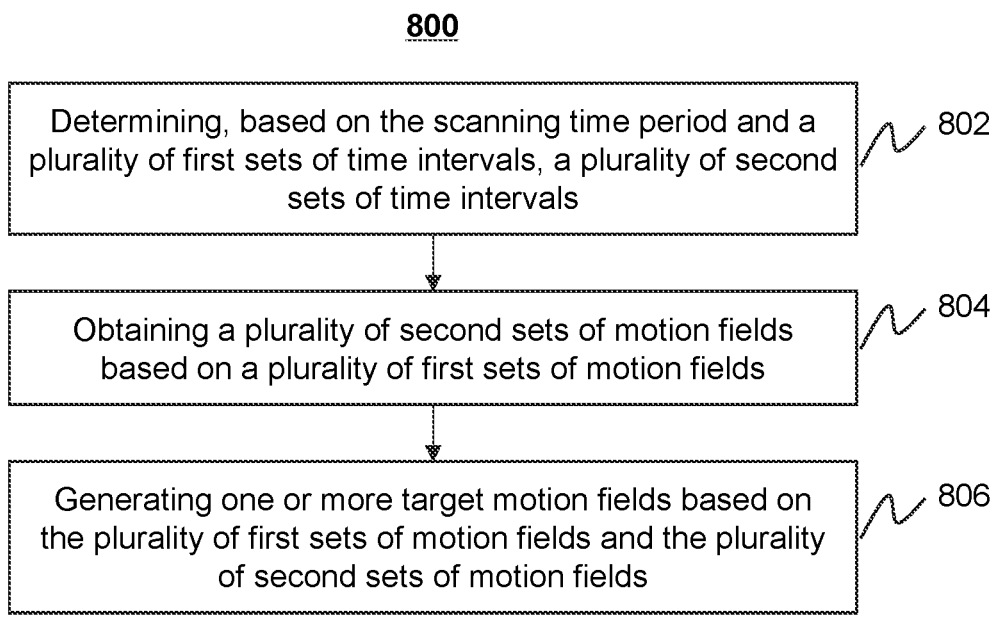
FIG. 8 is a flowchart illustrating an exemplary process for generating target motion fields based on a plurality of first sets of motion fields according to some embodiments of the present disclosure.

FIG. 8 is a flowchart illustrating an exemplary process for generating target motion fields based on a plurality of first sets of motion fields according to some embodiments of the present disclosure. In some embodiments, at least part of process 800 may be performed by the processing device 140 (implemented in, for example, the computing device 200 shown in FIG. 2). For example, the process 800 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 4). The operations of the illustrated process presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting. In some embodiments, operation 610 illustrated in FIG. 6 may be performed according to the process 800.

In 802, the processing device 140 (e.g., the generation module 420, or the second motion field generation unit 424) may determine a plurality of second sets of time intervals. In some embodiments, the second sets of time intervals may be determined based on the entire scanning time period (as illustrated in FIGS. 5-6) and a plurality of first sets of time intervals (e.g., the first sets of time intervals in which the plurality of first sets of MR image data are generated as illustrated in FIGS. 6-7). A second set of time intervals may refer to a time period in which no first set of imaging sequences is used. For example, the second set of time intervals may include a time period no imaging sequence is used (i.e., the object is not scanned). As another example, the second set of time intervals may include a time period a second set of imaging sequences is used to generate a second set of MR image data. Because the entire scanning time period includes the plurality of first sets of time intervals in which the plurality of first sets of MR image data are generated and a plurality of second sets of time intervals in which the plurality of second sets of MR image data are generated (or no MR image data are generated), the plurality of second sets of time intervals may be determined based on the scanning time period and the plurality of first sets of time intervals.

In 804, the processing device 140 (e.g., the generation module 420, or the second motion field generation unit 424) may obtain a plurality of second sets of motion fields based on the plurality of first sets of motion fields. In some embodiments, the second sets of motion fields may be obtained by generating, based on the plurality of first sets of motion fields, at least one second set of motion fields corresponding to each second set of time intervals of the plurality of second sets of time intervals. In some embodiments, a (or each) second set of motion fields may correspond to a respiratory phase. In some embodiments, one or more second sets of motion fields (or at least one second set of motion fields) may correspond to a second set of time intervals.

In some embodiments, at least a portion of the plurality of second sets of motion fields may be obtained by duplicating the first sets of motion fields. For example, one or more first sets of motion fields corresponding to one of the plurality of first sets of time intervals that is adjacent to a second set of time intervals may be directly designated as the at least one second set of motion fields corresponding to the second set of time intervals. For illustration purposes, referring to FIG. 9, the first set of motion fields (corresponding to the first sets of time intervals in which the MR image data represented by the region A of the band 903 are generated) may be designated as the second set of motion fields (corresponding to the second sets of time intervals in which the MR image data represented by the region B of the band 903 are generated or no MR image data are generated).

In some embodiments, at least a portion of the plurality of second sets of motion fields may be obtained by fitting the first sets of motion fields. For example, the at least one second set of motion fields corresponding to a second set of time intervals may be generated by fitting one or more first sets of motion fields corresponding to two of the plurality of first sets of time intervals that are adjacent to the second set of time intervals. For illustration purposes, referring to FIG. 9, a motion field may be generated by fitting the first sets of motion fields (corresponding to the first sets of time intervals in which the MR image data represented by the region A of the band 903 are generated) and another first set of motion fields (corresponding to the first sets of time intervals in which the MR image data represented by the region C of the band 903 are generated), and may be designated as the second set of motion fields (corresponding to the second sets of time intervals in which the MR image data represented by the region B of the band 903 are generated or no MR image data are generated).

In some embodiments, at least a portion of the plurality of second sets of motion fields may be obtained based on a similarity (e.g., a similarity of the motion curve) between the first sets of time intervals and the second sets of time intervals. Merely by way of example, the first sets of time intervals may include a first plurality of respiratory phases (which may be represented by respiratory phases R1 for illustration purposes), and the second sets of time intervals may include a second plurality of respiratory phases (which may be represented by respiratory phases R2 for illustration purposes). The respiratory phases R1 and the respiratory phases R2 may refer to same respiratory phases (e.g., an initial stage of inspiration) of different respiratory cycles. Segments of the motion curve corresponding to the respiratory phases R1 and the respiratory phases R2 may be determined. Further, a similarity between a segment of motion curve corresponding to each respiratory phase R1 and a segment of motion curve corresponding to a specific respiratory phase R2 may be determined, and thus a plurality of similarities between the respiratory phases R1 and the specific respiratory phase R2 may be obtained. A second set of motion fields corresponding to the specific respiratory phase R2 may be determined based on a weighted sum of the plurality of similarities. Accordingly, a plurality of second sets of motion fields corresponding to a plurality of second sets of time intervals may be determined. In some embodiments, the similarities may be determined based on the amplitudes, phases, and/or time differences, or other factor(s) relating to segments of motion curve between respiratory phases.

In 806, the processing device 140 (e.g., the generation module 420, or the target motion field generation unit 426) may generate the one or more target motion fields based on the plurality of first sets of motion fields and the plurality of second sets of motion fields.

In some embodiments, the plurality of first sets of motion fields and the plurality of second sets of motion fields may be designated as the one or more target motion fields. For illustration purposes, referring to FIG. 9, the plurality of first sets of motion fields (corresponding to the first sets of time intervals in which the MR image data represented by the regions A, C and/or E of the band 903 are generated) and the plurality of second sets of motion fields (corresponding to the second sets of time intervals in which the MR image data represented by the regions B, D and/or F of the band 903 are generated or no MR image data are generated) may be designated as the one or more target motion fields.

It should be noted that the above description of process 800 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, operations 802 and 804 may be integrated into a single operation. As another example, operation 802 may be omitted. In some embodiments, a fitting function may be obtained based on an artificial intelligence model and may be used to fit the plurality of first sets of motion fields to obtain the second sets of motion fields or obtain the one or more target motion fields directly.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, device, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method implemented on at least one machine each of which has at least one processor and at least one storage device for image processing, the method comprising:
    obtaining a plurality of first sets of magnetic resonance (MR) image data of an object generated based on a plurality of first sets of imaging sequences, the plurality of first sets of imaging sequences being sparse in a scanning time period;
    obtaining a motion curve of the object, the motion curve being associated with a physiological motion of the object in the scanning time period; and
    generating one or more target motion fields corresponding to the scanning time period based on the plurality of first sets of MR image data and the motion curve, including:
        generating a plurality of first sets of motion fields based on the plurality of first sets of MR image data and the motion curve;
        generating a plurality of second sets of motion fields based on the plurality of first sets of motion fields;
        generating the one or more target motion fields based on the plurality of first sets of motion fields and the plurality of second sets of motion fields;
        obtaining positron emission tomography (PET) image data of the object generated in the scanning time period; and
        generating one or more corrected PET images by correcting, based on the one or more target motion fields, the PET image data, wherein a generation of at least a portion of the PET image data is simultaneous to a generation of the plurality of first sets of MR image data.

2. The method of claim 1, further comprising:
    obtaining a plurality of second sets of MR image data of the object generated based on a plurality of second sets of imaging sequences, the plurality of second sets of imaging sequences being interleaved with the plurality of first sets of imaging sequences.

3. The method of claim 2, further comprising:
    generating one or more corrected MR images by correcting, based on the one or more target motion fields, the plurality of second sets of MR image data.

4. The method of claim 1, further comprising:
    obtaining a plurality of second sets of MR image data of the object generated based on a plurality of second sets of imaging sequences, wherein the plurality of first sets of imaging sequences are sparsely interspersed between the plurality of second sets of imaging sequences.

5. The method of claim 1, wherein the motion curve includes at least one of a respiratory motion curve or a cardiac motion curve.

6. The method of claim 1, wherein the PET image data include PET raw data or data corresponding to one or more PET images reconstructed based on the PET raw data.

7. The method of claim 1, wherein the generating one or more target motion fields corresponding to the scanning time period comprises:
    obtaining the plurality of first sets of motion fields by generating, based on the motion curve, at least one first set of motion fields corresponding to each first set of time intervals in which one first set of MR image data among the plurality of first sets of MR image data are generated; and
    generating the one or more target motion fields based on the plurality of first sets of motion fields.

8. The method of claim 7, wherein the motion curve includes a respiratory motion curve, and the generating, based on the motion curve, at least one first set of motion fields corresponding to each first set of time intervals in which one first set of MR image data among the plurality of first sets of MR image data is generated comprises:
    determining a plurality of respiratory phases of a respiratory motion of the object;
    determining a plurality of pieces of MR image data corresponding to the plurality of respiratory phases by determining, based on the plurality of first sets of MR image data and the respiratory motion curve, a piece of MR image data corresponding to each of the plurality of respiratory phases;
    reconstructing a plurality of images corresponding to the plurality of respiratory phases based on the plurality of pieces of MR image data; and
    generating the at least one first set of motion fields based on the plurality of images corresponding to the plurality of respiratory phases.

9. The method of claim 8, wherein the determining a plurality of respiratory phases of a respiratory motion of the object comprises:
    determining a plurality of first sets of time intervals in which the plurality of first sets of MR image data is generated;
    determining at least one portion of the respiratory motion curve corresponding to the plurality of first sets of time intervals; and
    determining the plurality of respiratory phases of the respiratory motion of the object based on the at least one portion of the respiratory motion curve.

10. The method of claim 8, wherein the determining a plurality of pieces of MR image data corresponding to the plurality of respiratory phases comprises:
    dividing the plurality of first sets of MR image data into the plurality of pieces of MR image data corresponding to the plurality of respiratory phases, based on the plurality of first sets of MR image data and the plurality of respiratory phases.

11. The method of claim 7, wherein the generating the one or more target motion fields based on the plurality of first sets of motion fields comprises:
    generating the one or more target motion fields by fitting the plurality of first sets of motion fields.

12. The method of claim 7, wherein the each first set of time intervals includes one or more respiratory cycles of the object.

13. The method of claim 1, wherein the generating a plurality of second sets of motion fields comprises:
    determining, based on the scanning time period and a plurality of first sets of time intervals in which the plurality of first sets of MR image data is generated, a plurality of second sets of time intervals; and
    obtaining the plurality of second sets of motion fields by generating, based on the plurality of first sets of motion fields, at least one second set of motion fields corresponding to each second set of time intervals of the plurality of second sets of time intervals.

14. The method of claim 13, wherein the generating, based on the plurality of first sets of motion fields, at least one second set of motion fields corresponding to each second set of time intervals of the plurality of second sets of time intervals comprises:
    designating one or more first sets of motion fields corresponding to one of the plurality of first sets of time intervals that is adjacent to the each second set of time intervals as the at least one second set of motion fields.

15. The method of claim 13, wherein the generating, based on the plurality of first sets of motion fields, at least one second set of motion fields corresponding to each second set of time intervals of the plurality of second sets of time intervals comprises:

generating the at least one second set of motion fields corresponding to the each second set of time intervals by fitting one or more first sets of motion fields corresponding to two of the plurality of first sets of time intervals that are adjacent to the each second set of time intervals.

16. The method of claim 13, wherein the generating the one or more target motion fields based on the plurality of first sets of motion fields and the plurality of second sets of motion fields comprises:

designating the plurality of first sets of motion fields and the plurality of second sets of motion fields as the one or more target motion fields.

17. A system for image processing, comprising:

at least one storage device storing a set of instructions; and at least one processor in communication with the storage device, wherein when executing the set of instructions, the at least one processor is configured to cause the system to perform operations including:

obtaining a plurality of first sets of magnetic resonance (MR) image data of an object generated based on a plurality of first sets of imaging sequences, the plurality of first sets of imaging sequences being sparse in a scanning time period;

obtaining a motion curve of the object, the motion curve being associated with a physiological motion of the object in the scanning time period; and generating one or more target motion fields corresponding to the scanning time period based on the plurality of first sets of MR image data and the motion curve, including:

generating a plurality of first sets of motion fields based on the plurality of first sets of MR image data and the motion curve;

generating a plurality of second sets of motion fields based on the plurality of first sets of motion fields;

generating the one or more target motion fields based on the plurality of first sets of motion fields and the plurality of second sets of motion fields;

obtaining positron emission tomography (PET) image data of the object generated in the scanning time period; and generating one or more corrected PET images by correcting, based on the one or more target motion fields, the PET image data, wherein a generation of at least a portion of the PET image data is simultaneous to a generation of the plurality of first sets of MR image data.

18. The system of claim 17, further comprising:

obtaining a plurality of second sets of MR image data of the object generated based on a plurality of second sets of imaging sequences, the plurality of second sets of imaging sequences being interleaved with the plurality of first sets of imaging sequences.

19. The system of claim 17, further comprising:

obtaining a plurality of second sets of MR image data of the object generated based on a plurality of second sets of imaging sequences, wherein the plurality of first sets of imaging sequences are sparsely interspersed between the plurality of second sets of imaging sequences.

20. A non-transitory computer readable medium storing instructions, the instructions, when executed by at least one processor, causing the at least one processor to implement a method comprising:

obtaining a plurality of first sets of magnetic resonance (MR) image data of an object generated based on a plurality of first sets of imaging sequences, the plurality of first sets of imaging sequences being sparse in a scanning time period;

obtaining a motion curve of the object, the motion curve being associated with a physiological motion of the object in the scanning time period; and generating one or more target motion fields corresponding to the scanning time period based on the plurality of first sets of MR image data and the motion curve, including:

generating a plurality of first sets of motion fields based on the plurality of first sets of MR image data and the motion curve;

generating a plurality of second sets of motion fields based on the plurality of first sets of motion fields;

generating the one or more target motion fields based on the plurality of first sets of motion fields and the plurality of second sets of motion fields;

obtaining positron emission tomography (PET) image data of the object generated in the scanning time period; and generating one or more corrected PET images by correcting, based on the one or more target motion fields, the PET image data, wherein a generation of at least a portion of the PET image data is simultaneous to a generation of the plurality of first sets of MR image data.

* * * * *